(12) United States Patent
Nakajima et al.

(10) Patent No.: US 8,383,130 B2
(45) Date of Patent: Feb. 26, 2013

(54) PARTIAL PEPTIDE OF LACRITIN

(75) Inventors: Takeshi Nakajima, Hyogo (JP); Mitsuyoshi Azuma, Hyogo (JP)

(73) Assignee: Senju Pharmaceutical Co., Ltd., Osaka-shi (JP)

( * ) Notice: Subject to any disclaimer, the term of this patent is extended or adjusted under 35 U.S.C. 154(b) by 224 days.

(21) Appl. No.: 12/922,084

(22) PCT Filed: Mar. 19, 2009

(86) PCT No.: PCT/JP2009/055489
§ 371 (c)(1), (2), (4) Date: Sep. 30, 2010

(87) PCT Pub. No.: WO2009/116639
PCT Pub. Date: Sep. 24, 2009

(65) Prior Publication Data
US 2011/0008891 A1    Jan. 13, 2011

(30) Foreign Application Priority Data
Mar. 19, 2008    (JP) .................................. 2008-071065

(51) Int. Cl.
*A61K 38/18* (2006.01)
*C07K 14/435* (2006.01)
*C07K 14/475* (2006.01)

(52) U.S. Cl. ..................... 424/198.1; 530/300; 530/324; 514/1.1

(58) Field of Classification Search .................. None
See application file for complete search history.

(56) References Cited

U.S. PATENT DOCUMENTS
2004/0081984 A1    4/2004 Laurie et al.

FOREIGN PATENT DOCUMENTS
| JP | 2004-536570 A | 12/2004 |
| WO | WO 02/065943 A2 | 8/2002 |
| WO | WO 2005/119899 A2 | 12/2005 |
| WO | WO 2008/033477 A1 | 3/2008 |

OTHER PUBLICATIONS

"Cells and Tissues" in Cell Biology: A Short Course, Second Edition. Stephen Bolsover et al. New Jersey: John Wiley & Sons, Inc., 2004, pp. 1-18.*
Skolnick et al. From genes to protein structure and function: novel applications of computational approaches in the genomic era. Trends in Biotech 18(1): 34-39, 2000.*
Bork, A. Powers and pitfalls in sequence analysis: the 70% hurdle. Genome Res 10: 398-400, 2000.*
Doerks et al. Protein annotation: detective work for function prediction. Trends in Genetics 14(6): 248-250, 1998.*
Smith et al. The challenges of genome sequence annotation or "The devil is in the details". Nature Biotech 15: 1222-1223, 1997.*
Brenner, S.E. Errors in genome function. Trends in Genetics 15(4): 132-133, 1999.*
Bork et al. Go hunting in sequence databases but watch out for the traps. Trends in Genetics. 12(10): 425-427, 1996.*
Wells. J.A. Additivity of mutational effects in proteins. Biochemistry 29 (37): 8509-8517, 1990.*
Ngo et al. Computational complexity, protein structure prediction, and the Levinthal paradox. The Protein Folding Problem and Tertiary Structure Prediction, pp. 492-495, 1994.*
Tokuriki et al. Stability effects of mutations and protein evolvability. Curr Opin Structural Biol 19: 596-604, 2009.*
Ma et al., *Experimental Eye Research*, 86(3): 457-458 (2008).
European Patent Office, Supplementary European Search Report for European Patent Application No. 09 72 2944.7-2403 (Jul. 25, 2011).
Frisch et al., *The Journal of Cell Biology*, 124(4): 619-626 (Feb. 1994).
Ma et al., *The Journal of Cell Biology*, 174(7): 1097-1106 (Sep. 25, 2006).
Sanghi et al., *Journal of Molecular Biology*, 310: 127-139 (2001).
Wang et al., *The Journal of Cell Biology*, 174(5): 689-700 (Aug. 28, 2006).

* cited by examiner

*Primary Examiner* — Bridget E Bunner
(74) *Attorney, Agent, or Firm* — Leydig, Voit & Mayer, Ltd.

(57) ABSTRACT

The invention provides a polypeptide comprising the amino acid sequence of SEQ ID NO: 1, which is a particular partial sequence of lacritin, and having an amino acid length of not more than 70 residues. The polypeptide of the invention can promote adhesion between a cell and an extracellular matrix, and can promote tear fluid secretion from lacrimal gland acinar cells.

21 Claims, No Drawings

```
                         SEQUENCE LISTING

<160> NUMBER OF SEQ ID NOS: 8

<210> SEQ ID NO 1
<211> LENGTH: 34
<212> TYPE: PRT
<213> ORGANISM: Homo sapiens

<400> SEQUENCE: 1

Gln Gly Thr Ala Lys Val Thr Ser Ser Arg Gln Glu Leu Asn Pro Leu
1               5                   10                  15

Lys Ser Ile Val Glu Lys Ser Ile Leu Leu Thr Glu Gln Ala Leu Ala
            20                  25                  30

Lys Ala

<210> SEQ ID NO 2
<211> LENGTH: 138
<212> TYPE: PRT
<213> ORGANISM: Homo sapiens

<400> SEQUENCE: 2

Met Lys Phe Thr Thr Leu Leu Phe Leu Ala Ala Val Ala Gly Ala Leu
1               5                   10                  15

Val Tyr Ala Glu Asp Ala Ser Ser Asp Ser Thr Gly Ala Asp Pro Ala
            20                  25                  30

Gln Glu Ala Gly Thr Ser Lys Pro Asn Glu Glu Ile Ser Gly Pro Ala
        35                  40                  45

Glu Pro Ala Ser Pro Pro Glu Thr Thr Thr Thr Ala Gln Glu Thr Ser
    50                  55                  60

Ala Ala Ala Val Gln Gly Thr Ala Lys Val Thr Ser Ser Arg Gln Glu
65                  70                  75                  80

Leu Asn Pro Leu Lys Ser Ile Val Glu Lys Ser Ile Leu Leu Thr Glu
                85                  90                  95

Gln Ala Leu Ala Lys Ala Gly Lys Gly Met His Gly Gly Val Pro Gly
            100                 105                 110

Gly Lys Gln Phe Ile Glu Asn Gly Ser Glu Phe Ala Gln Lys Leu Leu
        115                 120                 125

Lys Lys Phe Ser Leu Leu Lys Pro Trp Ala
    130                 135

<210> SEQ ID NO 3
<211> LENGTH: 35
<212> TYPE: PRT
<213> ORGANISM: Homo sapiens
```

-continued

```
<400> SEQUENCE: 3

Val Gln Gly Thr Ala Lys Val Thr Ser Ser Arg Gln Glu Leu Asn Pro
1               5                   10                  15

Leu Lys Ser Ile Val Glu Lys Ser Ile Leu Leu Thr Glu Gln Ala Leu
            20                  25                  30

Ala Lys Ala
        35

<210> SEQ ID NO 4
<211> LENGTH: 45
<212> TYPE: PRT
<213> ORGANISM: Homo sapiens

<400> SEQUENCE: 4

Gln Gly Thr Ala Lys Val Thr Ser Ser Arg Gln Glu Leu Asn Pro Leu
1               5                   10                  15

Lys Ser Ile Val Glu Lys Ser Ile Leu Leu Thr Glu Gln Ala Leu Ala
            20                  25                  30

Lys Ala Gly Lys Gly Met His Gly Gly Val Pro Gly Gly
        35                  40                  45

<210> SEQ ID NO 5
<211> LENGTH: 55
<212> TYPE: PRT
<213> ORGANISM: Homo sapiens

<400> SEQUENCE: 5

Gln Gly Thr Ala Lys Val Thr Ser Ser Arg Gln Glu Leu Asn Pro Leu
1               5                   10                  15

Lys Ser Ile Val Glu Lys Ser Ile Leu Leu Thr Glu Gln Ala Leu Ala
            20                  25                  30

Lys Ala Gly Lys Gly Met His Gly Gly Val Pro Gly Gly Lys Gln Phe
        35                  40                  45

Ile Glu Asn Gly Ser Glu Phe
    50                  55

<210> SEQ ID NO 6
<211> LENGTH: 33
<212> TYPE: PRT
<213> ORGANISM: Homo sapiens

<400> SEQUENCE: 6

Glu Ile Ser Gly Pro Ala Glu Pro Ala Ser Pro Pro Gly Thr Thr Thr
1               5                   10                  15

Thr Ala Gln Glu Thr Ser Ala Ala Ala Val Gln Gly Thr Ala Lys Val
            20                  25                  30

Thr

<210> SEQ ID NO 7
<211> LENGTH: 16
<212> TYPE: PRT
<213> ORGANISM: Homo sapiens

<400> SEQUENCE: 7

Gln Gly Thr Ala Lys Val Thr Ser Ser Arg Gln Glu Leu Asn Pro Leu
1               5                   10                  15

<210> SEQ ID NO 8
<211> LENGTH: 60
<212> TYPE: PRT
<213> ORGANISM: Homo sapiens
```

```
<400> SEQUENCE: 8

Glu Ile Ser Gly Pro Ala Glu Pro Ala Ser Pro Pro Glu Thr Thr Thr
1               5                   10                  15

Thr Ala Gln Glu Thr Ser Ala Ala Ala Val Gln Gly Thr Ala Lys Val
            20                  25                  30

Thr Ser Ser Arg Gln Glu Leu Asn Pro Leu Lys Ser Ile Val Glu Lys
        35                  40                  45

Ser Ile Leu Leu Thr Glu Gln Ala Leu Ala Lys Ala
    50                  55                  60
```

PARTIAL PEPTIDE OF LACRITIN

CROSS-REFERENCE TO RELATED APPLICATIONS

This application is the U.S. national phase of International Patent Application No. PCT/JP2009/055489, filed on Mar. 19, 2009, which claims priority to Japanese Patent Application No. 2008-071065, filed on Mar. 19, 2008.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 4,371 bytes ASCII (Text) file named "706911SequenceListing.txt," created Sep. 10, 2010.

TECHNICAL FIELD

The present invention relates to polypeptide having a particular partial sequence of lacritin which is a protein in the tear fluid. The polypeptide of the present invention can promote cell adhesion, particularly cell adhesion between a cell and an extracellular matrix. Furthermore, the polypeptide of the present invention can promote tear fluid secretion.

BACKGROUND ART

It is known that cell-extracellular matrix adhesion is involved in various functions such as cell survival, motility and the like. This is a process essential for controlling the normal development of individual, maintenance of tissues, or recovery from damage or infection. An abnormality in the signaling pathway based on such cell adhesion sometimes leads to abnormal development, circulatory diseases or transformation or metastasis of the cells.

In addition, it has been reported that when the cell-extracellular matrix adhesion is inhibited, the cells reach cell death called "anoikis", and therefore, adhesion to an extracellular matrix is important for the survival of the cells (see non-patent document 1).

Lacritin is a protein identified as a tear secretion promoting factor or a growth-factor-like protein (see patent documents 1 and 2 and non-patent document 2). For lacritin, the following 1) to 5) are reported:
1) Lacritin has an activity as a growth factor for a corneal epithelial cell and a lacrimal gland acinar cell.
2) Lacritin shows a promoting effect on tear protein secretion.
3) Lacritin is expressed in a cell derived from tissues such as the lacrimal gland, parotid gland, minor salivary gland, submandibular gland, thyroid gland, mammary gland and corneal epithelium.
4) Eyedrops containing lacritin are likely to be useful in the treatment of ocular diseases such as dry eye syndrome, Sjogren's syndrome, and corneal epithelial wounds.
5) Compounds that bind to lacritin or lacritin receptors can be screened for using a cell expressing a lacritin receptor with a lacritin-dependent calcium signal as an index.

In addition, it has been reported that lacritin or a peptide thereof partly defective in the both terminals has an action to promote division of salivary gland cells in a detection test of $^3$H-thymidine uptake (see non-patent document 3).

However, it has not been reported that lacritin or a fragment thereof (partial peptide) is involved in the cell-extracellular matrix adhesion. In addition, an action of a lacritin fragment to promote secretion of a tear protein from lacrimal gland acinar cells has not been reported.

patent document 1: WO02/065943
patent document 2: WO05/119899
non-patent document 1: Frisch, S. M. et al., Journal of Cell Biology 124, pp. 619-626 (1994)
non-patent document 2: Sanghi, S. et al., Journal of Molecular Biology 310, pp. 127-139 (2001)
non-patent document 3: Wang, J. et al. Journal of Cell Biology 174, pp. 689-700 (2006)

DISCLOSURE OF THE INVENTION

Problems to be Solved by the Invention

An object of the present invention is to provide a substance capable of promoting adhesion between a cell and an extracellular matrix, particularly a corneal epithelial cell and an extracellular matrix and/or a substance having an action to promote secretion of a tear protein from lacrimal gland acinar cells.

Means of Solving the Problems

The present inventors have conducted intensive studies in view of the above-mentioned problems, and found that a polypeptide having a particular partial sequence of lacritin can promote adhesion between a corneal epithelial cell and an extracellular matrix, and can further promote secretion of a tear protein from lacrimal gland acinar cells, which resulted in the completion of the present invention. Accordingly, the present invention is as follows.

[1] A polypeptide comprising the amino acid sequence of SEQ ID NO: 1 and having an amino acid length of not more than 70 residues.
[2] A polypeptide comprising the amino acid sequence of SEQ ID NO: 1 wherein 1 to 3 amino acids are deleted, substituted or added, and having an activity equivalent to that of the polypeptide of the above-mentioned [1] and an amino acid length of not more than 70 residues.
[3] The polypeptide of the above-mentioned [1], wherein the part other than the amino acid sequence of SEQ ID NO: 1 is comprised of a partial sequence of the amino acid sequence of SEQ ID NO: 2.
[4] A polypeptide consisting of the amino acid sequence of the polypeptide of the above-mentioned [3], wherein 1 to 3 amino acids are deleted, substituted or added, and having an activity equivalent to that of the polypeptide of the above-mentioned [3].
[5] The polypeptide of the above-mentioned [1], consisting of a partial sequence of the amino acid sequence of SEQ ID NO: 2.
[6] A polypeptide consisting of the sequence of the polypeptide of the above-mentioned [5], wherein 1 to 3 amino acids are deleted, substituted or added, and having an activity equivalent to that of the polypeptide of the above-mentioned [5].
[7] A polypeptide consisting of the amino acid sequence of any of SEQ ID NOs: 3-5.
[8] A polypeptide consisting of the amino acid sequence of any of SEQ ID NOs: 3-5 wherein 1 to 3 amino acids are deleted, substituted or added, and having an activity equivalent to that of the polypeptide of the above-mentioned [7].
[9] An agent for promoting cell adhesion, comprising the polypeptide of any one of the above-mentioned [1]-[8].

[10] A method of promoting cell adhesion, comprising contacting an effective concentration of the polypeptide of any one of the above-mentioned [1]-[8] with a cell.

[11] An agent for promoting secretion of a tear fluid, comprising the polypeptide of any one of the above-mentioned [1]-[8].

Effect of the Invention

The present invention can provide a novel polypeptide capable of promoting adhesion between a cell and an extracellular matrix, particularly a corneal epithelial cell and an extracellular matrix. The polypeptide of the present invention can prepare a corneal epithelial sheet, which functions stably for a long time by preventing cell dropout, by adding the polypeptide into a culture medium for preparation of a corneal epithelial sheet for transplantation. Furthermore, the present invention can provide a novel polypeptide capable of the promoting action of tear fluid secretion from the lacrimal gland acinar cells. A substance directly acting on the lacrimal gland and capable of the promoting action of tear fluid secretion can be a useful drug for the prophylaxis or treatment of dry eye or a disease accompanied by dry eye.

BEST MODE FOR CARRYING OUT THE INVENTION

One embodiment of the polypeptide of the present invention is a polypeptide comprising the amino acid sequence shown by the following SEQ ID NO: 1.

QGTAKVTSSRQELNPLKSIVEKSILLTEQALAKA (SEQ ID NO: 1)

The amino acid sequence of SEQ ID NO: 1 corresponds to the 69th-102nd of human-derived full-length lacritin (see GenBank/EBI data bank accession Nos. NM_033277 and ay005150 (genomic)) of SEQ ID NO: 2 consisting of 138 residues.

Furthermore, the polypeptide of the present invention may be a polypeptide comprising the amino acid sequence of SEQ ID NO: 1 wherein 1 to 3, preferably 1 or 2, more preferably 1, amino acid is deleted, substituted or added, as long as it has an activity equivalent to that of the aforementioned polypeptide.

amino acid sequence of SEQ ID NO: 1 wherein 1 to 3 amino acids are deleted, substituted or added). Examples of the any amino acid sequence include a partial sequence of the amino acid sequence of SEQ ID NO: 2 (mentioned below).

Preferably, the polypeptide of the present invention consists only of the partial sequence of the amino acid sequence of SEQ ID NO: 2 besides the amino acid sequence of SEQ ID NO: 1. The partial sequence of the amino acid sequence of SEQ ID NO: 2 means any partial sequence of the amino acid sequence of SEQ ID NO: 2 (amino acid sequence of lacritin), and may comprise a part or all of the amino acid sequence of SEQ ID NO: 1. The partial sequence of the amino acid sequence of SEQ ID NO: 2 can be added to the N-terminal side, the C-terminal side, or both the N-terminal side and C-terminal side of the amino acid sequence of SEQ ID NO: 1.

When the partial sequence of the amino acid sequence of SEQ ID NO: 2 is added to both the N-terminal side and the C-terminal side of the amino acid sequence of SEQ ID NO: 1, they may be continuous to each other in the amino acid sequence of SEQ ID NO: 2, may be non-continuous, or may be partly or entirely overlapping with each other.

Here, the obtained polypeptide may have an amino acid sequence wherein 1 to 3, preferably 1 or 2, more preferably 1, amino acid is deleted, substituted or added, as long as it has an activity equivalent to that of said polypeptide, i.e., as long as it maintains a promoting action of cell adhesion and/or a promoting action of tear fluid secretion of said polypeptide.

The polypeptide of the present invention is more preferably a polypeptide with not more than 70 residues comprising the amino acid sequence of SEQ ID NO: 1, and constitutes, as a whole, a continuous partial peptide of lacritin. That is, one embodiment of the polypeptide of the present invention is a partial peptide of lacritin of not more than 70 residues, consisting of a continuous amino acid sequence of a part of the 33rd-138th of the amino acid sequence of SEQ ID NO: 2.

Here, the obtained polypeptide may have an amino acid sequence wherein 1 to 3, preferably 1 or 2, more preferably 1, amino acid is deleted, substituted or added as long as it has an activity equivalent to that of said polypeptide, i.e., as long as it maintains a promoting action of cell adhesion and/or a promoting action of tear fluid secretion of said polypeptide.

A more preferable embodiment of the polypeptide of the present invention is a polypeptide consisting of the amino acid sequence consisting of any of the following SEQ ID NOs: 3-5.

VQGTAKVTSSRQELNPLKSIVEKSILLTEQALAKA (SEQ ID NO: 3)

QGTAKVTSSRQELNPLKSIVEKSILLTEQALAKAGKGMHGGVPGG (SEQ ID NO: 4)

QGTAKVTSSRQELNPLKSIVEKSILLTEQALAKAGKGMHGGVPGGKQFIENGSEF (SEQ ID NO: 5)

The amino acid length of the polypeptide of the present invention is generally not more than 70 residues, preferably not more than 60 residues, particularly preferably 32 to 58 residues, most preferably 34 to 55 residues. It is also preferably 35 to 55 residues.

As long as the amino acid sequence of the polypeptide of the present invention comprises the amino acid sequence of SEQ ID NO: 1 (or the amino acid sequence of SEQ ID NO: 1 wherein 1 to 3 amino acids are deleted, substituted or added), the rest thereof may be any amino acid sequence. The any amino acid sequence may be present at the N-terminal side, the C-terminal side, or both the N-terminal side and C-terminal side of the amino acid sequence of SEQ ID NO: 1 (or the The amino acid sequences of SEQ ID NO: 3, SEQ ID NO: 4 and SEQ ID NO: 5 correspond to the 68th-102nd, 69th-113th or 69th-123rd of the amino acid sequence of lacritin (SEQ ID NO: 2), respectively. In other words, the polypeptide of the present invention consisting of the amino acid sequence of SEQ ID NOs: 3-5 is a partial sequence of lacritin.

A still another preferable embodiment of the polypeptide of the present invention is a polypeptide consisting of the amino acid sequence consisting of the following SEQ ID NO: 8.

EISGPAEPASPPETTTTAQETSAAAVQGTAKVTSSRQELNPLKSIVEKSILLTEQALAKA (SEQ ID NO: 8)

The amino acid sequence of SEQ ID NO: 8 corresponds to the 43rd-102nd of the amino acid sequence of lacritin (SEQ ID NO: 2). In other words, the polypeptide of the present invention consisting of the amino acid sequence of SEQ ID NO: 8 is a partial peptide of lacritin.

The polypeptide of the present invention, which is a partial peptide of lacritin as mentioned above, may have an amino acid sequence wherein 1 to 3, preferably 1 or 2, more preferably 1, amino acid is deleted, substituted or added as long as it has an activity equivalent to that of the polypeptide, i.e., as long as it maintains a promoting action of cell adhesion and/or a promoting action of tear fluid secretion of the polypeptide.

In the present specification, the "amino acid" generally means "natural amino acid". However, it may be "non-natural amino acid" as long as it satisfies the object of the present invention. Here, the "natural amino acid" means an L-isomer of natural amino acid. The natural amino acid includes glycine, alanine, valine, leucine, isoleucine, serine, methionine, threonine, phenylalanine, tyrosine, tryptophan, cysteine, proline, histidine, aspartic acid, asparagine, glutamic acid, glutamine, arginine, ornithine and lysine. Unless otherwise specified, all amino acids in the present specification are L-forms. However, an embodiment using amino acid in a D-form is also within the scope of the present invention. Here, the "non-natural amino acid" means amino acid generally absent in a protein. Examples of the non-natural amino acid include D-form of norleucine, para-nitrophenylalanine, homophenylalanine, para-fluorophenylalanine, 3-amino-2-benzylpropionic acid or homoarginine and D-phenylalanine.

In the present specification, the "partial peptide" is a polypeptide consisting of a part of the amino acid sequence of lacritin of SEQ ID NO: 2.

In the present specification, the "deletion of amino acid" means removal of constituent amino acid from any position of the amino acid sequence.

In the present specification, the "substitution of amino acid" means substitution of the constituent amino acid with other amino acid at any position of the amino acid sequence. As the substitution of the amino acid, conservative substitution is preferable. The conservative substitution means a substitution such that amino acid is substituted by other amino acid having similar property, due to which those of ordinary skill in the art in the peptide chemistry expect the secondary structure and hydropathy property of polypeptide do not change substantially. As groups of amino acids in conservative substitution with each other, the following are generally known: (1) glycine, asparagine, glutamine, cysteine, serine, threonine and tyrosine; (2) alanine, valine, leucine, isoleucine, proline, phenylalanine, methionine and tryptophan; (3) glycine, alanine, serine, threonine and methionine; (4) leucine, isoleucine and valine; (5) glutamine and asparagine; (6) glutamic acid and aspartic acid; (7) arginine, lysine and histidine; (8) phenylalanine, tryptophan and tyrosine.

In the present specification, the "addition of amino acid" means addition of any amino acid to any position of an amino acid sequence, and includes insertion of an amino acid.

As mentioned above, the polypeptide of the present invention may have an amino acid sequence wherein 1 to 3, preferably 1 or 2, more preferably 1, amino acid is deleted, substituted or added as long as it has an activity equivalent to that of said polypeptide, and such polypeptide is also within the scope of the present invention. Here, "having an activity equivalent" means the presence of not less than about 80%, preferably not less than about 90%, of a promoting action of cell adhesion of the polypeptide before deletion, substitution or addition of the amino acid. As the promoting action of cell adhesion, an action capable of promoting adhesion between a cell and an extracellular matrix can be recited as an example. This action can be assayed as described in the below-mentioned Examples by adding a test polypeptide onto a plate coated with a suitable extracellular matrix, forming a layer of corneal epithelial cells thereon, incubating the cells for a given time, and counting the adhered cells. Alternatively, "having an activity equivalent" means the presence of not less than about 80%, preferably not less than about 90%, of a promoting action of tear fluid secretion of the polypeptide before deletion, substitution or addition of the amino acid. As the promoting action of tear fluid secretion, an action to promote secretion of a tear protein (e.g., lactoferrin) from the lacrimal gland acinar cell can be recited as an example. This action can be assayed as described in the below-mentioned Examples by culturing a suitable lacrimal gland acinar cell, adding a test polypeptide to a medium therefor, and quantifying the tear protein secreted in the medium.

In addition, each of the above-mentioned polypeptides may be a derivative wherein an N-terminal amino group, a C-terminal carboxyl group or a functional group of amino acid side chain is chemically modified within the range the activity thereof is not influenced. Examples of the derivatization include addition of a protecting group to an amino group (e.g., acetylation, formylation, Boc-ation, Fmoc-ation), esterification of a carboxyl group (ethylation and the like) and the like. When glutamine is present at the N-terminal, the side chain may be ring-closed to give pyroglutamic acid.

Each polypeptide may be in the form of a salt according to a known method. As the salt of the polypeptide, a pharmacologically acceptable salt with a base (for example, alkali metal) or a salt with an acid and a pharmacologically acceptable acid addition salt is particularly preferable. Examples of the pharmacologically acceptable acid addition salt include salts with inorganic acids (e.g., hydrochloric acid, phosphoric acid, hydrobromic acid, sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

The polypeptide of the present invention can be produced by a conventional chemical synthesis method, a recombination DNA technique or the like.

When the polypeptide of the present invention is produced by a chemical synthesis method, it can be produced according to a known peptide synthesis method. Examples of the peptide synthesis method include solid phase synthesis process, liquid phase synthesis process and the like, with preference given to solid phase synthesis process. Example of the solid phase synthesis process includes Fmoc method. The Fmoc method is a method of protecting an α-amino group with a 9-fluorenylmethoxycarbonyl (Fmoc) group, and protecting a side chain functional group with a t-butyl alcohol protecting group, wherein an Fmoc amino acid is condensed while deprotecting an Fmoc group with piperidine, which is a secondary amine, and the side chain protecting group is finally removed by weak acid such as trifluoroacetic acid. That is, a series of operations of selective removal of α-amino-protecting group and condensation of the protected amino acid is repeated from the C-terminal side of the peptide to be synthesized to construct a protected peptide chain, and the protecting group of the side chain functional group is removed to give the object peptide.

In the solid phase peptide synthesis method, synthesis by an automatic peptide synthesis apparatus is also generally used (e.g., "Shin-Seikagaku Jikken-Koza vol. 1, protein IV" (1992) edited by the Japan Biochemical Learned Society, Tokyo Kagaku Dojin; "The Peptides: Analysis, Synthesis, Biology" Vol. 1-5, ed. by E. Gross, J. Meienhofer; Vol. 6-9, ed. by S. Udenfriend, J. Meienhofer, Academic Press, New York (1979-1987)).

When the polypeptide of the present invention is produced by a recombinant DNA technique, for example, primers are designed based on the base sequence of cDNA encoding the polypeptide and, using a suitable cDNA library as a template, the object sequence is amplified by polymerase chain reaction (PCR), whereby a cDNA encoding the polypeptide can be produced. Such PCR method is well known in the pertinent technical field and described, for example, in "PCR Protocols, A Guide to Methods and Applications", Academic. Press, Michael, et al., eds., 1990. Then, a DNA encoding the polypeptide of the present invention is incorporated into a suitable expression vector, which is then introduced into either eucaryote or prokaryote, and each chain is expressed to give the desired polypeptide. Examples of the host cell usable for expression of the polypeptide of the present invention include, but are not limited to, prokaryote hosts such as *Escherichia coli, Bacillus subtilis* and the like, and eucaryote hosts such as yeast, fungi, insect cell, mammalian cell and the like. Vector is a single strand or double stranded nucleic acid molecule that can be transfected into a cell and is replicatable in the cell genome or independently of the cell genome. An expression vector contains a promoter region that drives DNA expression, and may further contain a transcription and translation regulating sequence, for example, TATA box, capping sequence, CAAT sequence, 3' non-coding region, enhancer and the like. Examples of the promoter to be used in a prokaryote host include bla promoter, cat promoter and lacZ promoter, and that to be used in an eucaryote host include promoter of mouse metallothionein I gene sequence, herpes virus TK promoter, SV40 early promoter, yeast glycolytic enzyme gene sequence promoter and the like. Examples of the vector include, but are not limited to, pBR322, pUC118, pUC119, λgt10, λgt11, pMAM-neo, pKRC, BPV, vaccinia, SV40, 2-micron and the like.

Expression vector preferably contains one or more markers so that a host cell containing the vector can be selected. As a marker, those affording nutrition to a complementing auxotrophic host, antibiotic resistance (for example, ampicillin, tetracycline, neomycin, hygromycin, geneticin etc.) or heavy metal resistance (for example, copper) can be used.

Furthermore, a vector can be constructed such that the polypeptide of the present invention is secreted and expressed using a signal sequence or the polypeptide of the present invention is expressed in the form of a fusion polypeptide with different polypeptide. Using a fusion polypeptide, the stability of the polypeptide can be improved or purification can be facilitated. Construction of such an expression vector is well known in the pertinent technical field.

A vector constructed to express the polypeptide of the present invention can be introduced into a suitable host cell by transformation, transfection, conjugation, protoplast fusion, electroporation, particle gun technique, calcium phosphate precipitation, direct microinjection and the like. The polypeptide of the present invention can be obtained by growing a cell containing the vector in a suitable medium to produce the polypeptide of the present invention, recovering a desired recombinant polypeptide from the cell or medium, and purifying the polypeptide.

The polypeptide of the present invention can also be produced by entering the modification, by a known means such as Kunkel method, a Gapped duplex method and the like or a method analogous thereto, into the position corresponding to the amino acid deleted, substituted or added, to give a cDNA encoding the polypeptide, and subjecting the gene to a recombinant DNA technique similar to the aforementioned recombinant DNA techniques. A mutation can be introduced into the gene by, for example, using a mutation introduction kit based on a site-specific mutation induction method (for example, Mutant-K (Takara Bio Inc.), Mutant-G (Takara Bio Inc.)) and the like or LA PCR in vitro Mutagenesis series kit of Takara Bio Inc.

The polypeptide of the present invention obtained as mentioned above can be isolated and purified by a known method. Examples of known isolation and purification methods include salting out, solvent precipitation, dialysis, ultrafiltration, gel filtration, SDS-polyacrylamide gel electrophoresis, ion exchange chromatography, affinity-chromatography, reversed-phase high performance liquid chromatography, isoelectric focusing and the like.

The thus-obtained polypeptide of the present invention promotes adhesion between a cell and an extracellular matrix, particularly a corneal epithelial cell and an extracellular matrix. The following explains its specific use.

(1) Culture Medium Containing the Polypeptide of the Present Invention for Preparation of Corneal Epithelial Sheet The polypeptide of the present invention can particularly promote adhesion between a corneal epithelial cell and a base during preparation of a corneal epithelial sheet for transplantation, due to the promoting effect on the adhesion between a corneal epithelial cell and an extracellular matrix.

The corneal epithelial sheet is a substitute for living cornea and used for the treatment of cornea opacity to recover eyesight and the like. It is used for the treatment of a refractory cornea epithelial disease such as stevens-johnson syndrome, chemical trauma and the like. A corneal epithelial sheet is prepared by, for example, adding a cell such as a corneal epithelial cell and the like on a base such as amniotic membrane, collagen sheet and the like in a serum-containing medium, culturing the cell, and layering by coculture with 3T3 fibroblast, air-lifting and the like (Ophthalmology, vol. 42, No. 3, pages 245-250, 2000). As a method for preparation of a corneal epithelial sheet, known methods described in WO03/043542, JP-A-2004-298447, JP-A-2004-261533, JP-A-2002-331025 and the like are applied.

In the production method of the corneal epithelial sheet, a known base used for the production of a corneal epithelial sheet can be used, and any of a base derived from a living organism and an artificially prepared base can be used. Specifically, as a base derived from a living organism, amniotic membrane can be mentioned, and as an artificial base, a collagen sheet can be mentioned. The amniotic membrane covers the uterus and the outermost layer of the placenta, and is discharged from the body with the placenta during childbirth.

As a culture medium to be used for the cell culture, known culture media used for the production of a corneal epithelial sheet, such as EpiLife medium (manufactured by Cascade Biologics Inc.), DMEM/F12 medium (manufactured by Invitrogen Corporation), DMEM medium (manufactured by Invitrogen Corporation) and the like can be used, and the culture medium can contain a known serum. While the culture temperature is not particularly limited as long as the above-mentioned cells can grow well, it is generally about 15° C.-45° C. While the culture time is not particularly limited as long as the above-mentioned cell can grow well, it is generally about 1-30 days.

The polypeptide of the present invention added to a culture medium for the preparation of the corneal epithelial sheet can be an active ingredient for promoting adhesion between a corneal epithelial cell and a base. The concentration of polypeptide in a culture medium is generally 0.0001 w/v %-0.1 w/v %, preferably 0.001 w/v %-0.01 w/v %. The polypeptide of the present invention promotes fixation between an extracellular matrix of the base and a corneal epithelial cell, and enables preparation of a robust corneal epithelial sheet, which functions stably for a long time by preventing cell dropout.

(2) Medicament Containing the Polypeptide of the Present Invention

Since the polypeptide of the present invention promotes adhesion between a cell and an extracellular matrix, it is useful as an agent for promoting cell adhesion. The agent for promoting adhesion of the present invention is used for a cell (e.g., corneal epithelial cell, corneal endothelium cell, conjunctival cell and the like) derived from a mammal (e.g., rat, mouse, guinea pig, bird, sheep, horse, bovine, swine, monkey, chimpanzee, human etc.), preferably a corneal epithelial cell derived from human. The extracellular matrix is not particularly limited as long as it can adhere to a cell and includes (1) fibrous protein such as collagen, elastin and the like, (2) cell adhesion glycoprotein such as fibronectin, laminin, vitronectin and the like, (3) glycoconjugate such as glycosaminoglycans including heparin, hyaluronic acid, chondroitin sulfate and the like, and the like, as well as basal lamina (e.g., Bowman's membrane, Descemet's membrane, amniotic membrane and the like) comprised of these extracellular matrices.

It has been reported that cell adhesion to an extracellular matrix is important for cell survival (Frisch, S. M. et al., J. Cell Biol. 1994, 124, 619., Porcu, M., et al., Cornea 2007, 26, 73.). In the cornea, inhibition of cell adhesion due to the disappearance of laminin 5, which is one of the extracellular matrices, has also been reported to enhance death of corneal epithelial cells. Since the polypeptide of the present invention promotes adhesion of a corneal epithelial cell to the basal lamina (Bowman's membrane and the like) of corneal epithelium comprised of the extracellular matrix, it suppresses death of corneal epithelial cells on the surface layer of the eyes. Moreover, it is known that cell motilities consisting of division, migration (extension) and adhesion are involved in the repair of the corneal epithelium (Suzuki, K. et al., Prog. Retin. Eye Res. 2003, 22, 113). The polypeptide of the present invention promotes adhesion process in the cell motility, thereby promoting repair of corneal epithelial injury (i.e., wound or defect).

Therefore, a medicament containing the polypeptide of the present invention is useful for the treatment of a corneal epithelial disorder. As a specific disease causing a corneal epithelial disorder, keratitis due to physical or chemical stimulation, allergy, bacterial or fungal or virus infection and the like, corneal ulcer, corneal epithelial detachment (corneal erosion), corneal epithelial edema, corneal burn, cornea corrosion due to chemical substance and the like, dry eye, xerophthalmia, chronic superficial keratitis, superficial punctate keratopathy, corneal epithelial erosion, persistent corneal epithelial defects and the like can be mentioned. The polypeptide of the present invention is particularly useful for the treatment of a corneal epithelial disorder associated with these diseases.

In addition, the polypeptide of the present invention has a promoting action of tear fluid secretion from lacrimal gland acinar cells. Tear fluid covers eyeball surface composing of cornea and conjunctiva, maintains wettability of the keratoconjunctiva, and prevents drying. In recent years, however, an increasing number of people complain about various symptoms such as tired feeling, feeling of foreign substance, i.e., dry eye syndrome, due to dried cornea-conjunctiva surface associated with tear fluid decreases, dry eye during wearing contact lenses, or dry eye during operation of office automation equipment and the like. Dry eye sometimes accompany corneal epithelial disorder, cornea epithelial erosion and the like due to disorder of corneal epithelial cells and, in serious cases, may develop corneal ulcer or ophthalmic infection. To alleviate such various symptoms associated with drying, an artificial tear fluid mainly containing salts such as sodium chloride and the like, and eye drops containing hydroxyethylcellulose, chondroitin sulfate or hyaluronic acid and the like are used. As the situation stands, however, a satisfactory agent has not been developed as yet. Although such symptomatic therapy can alleviate symptoms, it is not a causal therapy for a basic treatment. Tear fluid is considered to have, based on its inherent function, a therapeutic effect on keratoconjunctival disorders due to dry eye. Therefore, a substance that directly acts on the lacrimal gland to promote tear fluid secretion is expected to be a useful prophylactic or therapeutic drug for dry eye and diseases associated with dry eye.

While the dosage form of a pharmaceutical product containing the polypeptide of the present invention is not particularly limited, preferred are eye drops, eye washes, eye ointment, tablet and the like, and more preferred are eye drops and eye ointment. These can be prepared by using a technique widely used. For example, eye drops can be prepared by appropriately blending additives such as isotonicity agent, buffering agent, pH adjuster, solubilizer, thickener, stabilizer, preservative and the like. In addition, stable eye drops can also be obtained by adding pH adjuster, thickener, dispersing agent and the like and suspending a drug.

Examples of the isotonicity agent include glycerol, propylene glycol, sodium chloride, potassium chloride, sorbitol, mannitol and the like.

Examples of the buffering agent include phosphoric acid, phosphate, citric acid, acetic acid, E-aminocaproic acid, tromethamol and the like.

Examples of the pH adjuster include hydrochloric acid, citric acid, phosphoric acid, acetic acid, sodium hydroxide, potassium hydroxide, boric acid, borax, sodium carbonate, sodium hydrogen carbonate and the like.

Examples of the solubilizer include polysorbate 80, polyoxyethylene hydrogenated castor oil 60, macrogol 4000 and the like.

Examples of the thickener and dispersing agent include cellulose polymers such as hydroxypropylmethylcellulose, hydroxypropylcellulose and the like, polyvinyl alcohol, polyvinylpyrrolidone and the like. Moreover, examples of the stabilizer include edetic acid, sodium edetate and the like.

Examples of the conventional preservative include sorbic acid, potassium sorbate, benzalkonium chloride, benzethonium chloride, methyl p-hydroxybenzoate, propyl p-hydroxybenzoate, chlorobutanol and the like. These preservatives may also be used in combination.

Eye drops containing the polypeptide of the present invention desirably has a pH of 4-8, and an osmotic pressure ratio of around 1.

In a pharmaceutical product containing the polypeptide of the present invention, the concentration of the polypeptide of the present invention can be set according to the symptom, age and the like and is not particularly limited. For example, when the polypeptide of the present invention is contained in eye drops, eye washes and the like, it is 0.001 w/v %-1 w/v %, preferably 0.05 w/v %-0.5 w/v %. The dose in the case of eye drops is, for example, one drop to several drops per instillation, which is given once to several times per day. Eye drops may be a general instillation solution, or an instillation solution to be dissolved when in use.

A pharmaceutical product containing the polypeptide of the present invention as an active ingredient can be used for, for example, mammals (e.g., rat, mouse, guinea pig, bird, sheep, horse, bovine, swine, monkey, chimpanzee, human etc.) and the like.

EXAMPLES

The present invention is explained in detail in the following by referring to Examples, which are not to be construed as limitative.

Example 1

Synthesis of Polypeptide

Polypeptide was synthesized by a solid phase synthesis process. To be specific, a fluorenylmethoxycarbonyl (Fmoc) group was introduced into amino acid and the amino acid was supported by a resin. Then, an amide bond formation reaction was performed using dichloromethane as a solvent, and 2-(1H-benzotriazol-1-yl)-1,1,3,3-tetramethyluronium (HBTU) and N-methylpyrrolidone (NMP) as coupling reagents. The protecting group was eliminated by using DMF/20% piperidine. The obtained product was purified by high performance liquid chromatography (column: ODS, solvent: water/acetonitrile/0.05% TFA). As a result, polypeptides 1-3 consisting of the following amino acid sequences were obtained.

```
polypeptide 1:
VQGTAKVTSSRQELNPLKSIVEKSILLTEQALAKA  (SEQ ID NO: 3)
``` white powder MALDI-TOF-MS Calcd.: 3750.13. Found: 3752.27;

Purity (HPLC A/A %) 96.207%

```
polypeptide 2:
                                       (SEQ ID NO: 4)
QGTAKVTSSRQELNPLKSIVEKSILLTEQALAKAGKGMHGGVPGG
``` white powder MALDI-TOF-MS Calcd.: 4588.35. Found: 4590.14;

Purity (HPLC A/A %) 96.88% polypeptide 3:

```
QGTAKVTSSRQELNPLKSIVEKSILLTEQALAKAGKGMHGGVPGGKQFIENGSEF(SEQ ID NO: 5)
``` white powder MALDI-TOF-MS Calcd.: 5768.64. Found: 5767.61;

Purity (HPLC A/A %) 95.15%

Example 2

Synthesis of Polypeptide

Polypeptide was synthesized by a solid phase synthesis process. To be specific, a fluorenylmethoxycarbonyl (Fmoc) group was introduced into amino acid and the amino acid was supported by a resin. And an amide bond formation reaction was performed using dichloromethane as a solvent, and 2-(1H-benzotriazol-1-yl)-1,1,3,3-tetramethyluronium (HBTU) and N-methylpyrrolidone (NMP) as coupling reagents. The protecting group was eliminated by using DMF/20% piperidine. The obtained product was purified by high performance liquid chromatography (column: ODS, solvent: water/acetonitrile/0.05% TFA). As a result, polypeptides 6 and 7 consisting of the following amino acid sequences were obtained.

```
polypeptide 6:
QGTAKVTSSRQELNPLKSIVEKSILLTEQALAKA (SEQ ID NO: 1)
``` white powder MALDI-TOF-MS Calcd.: 3653.27. Found: 3652.28;

Purity (HPLC A/A %) 99.26% polypeptide 7:

```
EISGPAEPASPPETTTTAQETSAAAVQGTAKVTSSRQELNPLKSIVEKSILLTEQALAKA(SEQ ID NO: 8)
``` white powder MALDI-TOF-MS Calcd.: 6148.92. Found: 6146.82;

Purity (HPLC A/A %) 87.47%

Comparative Example 1

In the same manner as in Example 1 above, polypeptides 4 and 5 consisting of the following amino acid sequences were obtained.

```
polypeptide 4:
EISGPAEPASPPETTTTAQETSAAAVQGTAKVT   (SEQ ID NO: 6)
``` white powder MALDI-TOF-MS Calcd.: 3197.56. Found: 3199.98;

Purity (HPLC A/A %) 99.53%

```
polypeptide 5: QGTAKVTSSRQELNPL      (SEQ ID NO: 7)
``` white powder MALDI-TOF-MS Calcd.: 1728.94. Found: 1728.82;

Purity (HPLC A/A %) 98.01%

Experimental Example 1

Promoting Effect by Partial Peptide of Lacritin on Adhesion of Human Corneal Epithelial Cell to Extracellular Matrix An extracellular matrix solution (10 μg/mL, collagen type IV: Becton, Dickinson and Company) was added to a 96 well plate (Iwaki Glass Company, Limited). The solution was incubated at 37° C. for 1 hr to coat the plate with the extracellular matrix. After the redundant extracellular matrix solution was removed, 0.1% BSA solution (Sigma-Aldrich Co.) was added to block the region not coated with the extracellular matrix. Successively, the BSA solution was removed and the plate was washed twice with PBS, and polypeptides 1-5 (concentration 100 μg/mL) synthesized in Example 1 and Comparative Example 1 were added by 50 μL per well. Furthermore, established human corneal epithelial cells (HCE-T:

can be prepared by the method described in Invest Ophthalmol Vis Sci. 1995, 36, 614) were cultured overnight under serum-free conditions and added to the plate at $2\times10^4$ cells/100 µL DMEM/F12 medium/well. The plate was incubated at 37° C. for 20 min to allow adhesion of the cells to the plate. The number of the adhered cells was counted by MTT assay (DOJINDO LABORATORIES). The cell adhesion ratio was calculated with no addition of polypeptide as 100% and is shown in Table 1.

TABLE 1

| | amino acid No. in lacritin | number of amino acid residues | cell adhesion rate (%) |
|---|---|---|---|
| polypeptide 1 | 68-102 | 35 | 147 |
| polypeptide 2 | 69-113 | 45 | 134 |
| polypeptide 3 | 69-123 | 55 | 147 |
| polypeptide 4 | 43-75 | 33 | 100 |
| polypeptide 5 | 69-84 | 16 | 98 |

As is clear from Table 1, polypeptides 1-3, which contain the amino acid sequence of SEQ ID NO: 1, were confirmed to have an activity to promote cell adhesion between a corneal epithelial cell and an extracellular matrix.

Experimental Example 2

Promoting Effect by Partial Peptide of Lacritin on Adhesion of Human Corneal Epithelial Cell to Extracellular Matrix An extracellular matrix solution (10 µg/mL, collagen type IV: Becton, Dickinson and Company) was added to a 96 well plate (Iwaki Glass Company, Limited). The solution was incubated at 37° C. for 1 hr to coat the plate with the extracellular matrix. After the redundant extracellular matrix solution was removed, 0.1% BSA solution (Sigma-Aldrich Co.) was added to block the region not coated with the extracellular matrix. Successively, the BSA solution was removed and the plate was washed three times with PBS, and polypeptides 4, 6 and 7 synthesized in Example 2 and Comparative Example 1 were suspended in PBS to a final concentration of 10 µM, and the suspension was added by 50 µL per well. Furthermore, established human corneal epithelial cells (HCE-T: can be prepared by the method described in Invest Ophthalmol Vis Sci. 1995, 36, 614) were cultured overnight under serum-free conditions and added to the plate at $2\times10^4$ cells/100 µL DMEM/F12 medium/well. The plate was incubated at 37° C. for 25 min to allow adhesion of the cells to the well. The number of the adhered cells was counted by MTT assay (DOJINDO LABORATORIES). The cell adhesion ratio was calculated with no addition of polypeptide as 100% and is shown in Table 2.

TABLE 2

| | amino acid No. in lacritin | number of amino acid residues | cell adhesion rate (%) |
|---|---|---|---|
| polypeptide 4 | 43-75 | 33 | 107 |
| polypeptide 6 | 69-102 | 34 | 160 |
| polypeptide 7 | 43-102 | 60 | 190 |

Experimental Example 3

Promoting Effect by Partial Peptide of Lacritin on Secretion of Tear Protein from Monkey Lacrimal Gland Acinar Cells Monkey lacrimal gland was chopped in a DMEM/F12 medium (Invitrogen Corporation) and treated with HBSS (Invitrogen Corporation) containing 0.76 mg/mL EDTA (Sigma-Aldrich Co.) and DMEM/F12 medium containing 200 U/mL collagenase A (Roche), 698 U/mL Hyarulonidase (Worthington Biochemical Corporation) and 10 U/mL DNase (Roche Diagnostics K.K.), and the cells were isolated. $1\times10^6$ cells were sown on a 6 well plate (ASAHI GLASS CO., LTD.) coated with 0.01 mg/cm$^2$ Collagen I (Becton, Dickinson and Company), and cultured in a $CO_2$ incubator at 37° C. overnight. The next day, the medium was changed to a supplement-free DMEM/F12 medium and the cells were pre-incubated at 37° C. for 30 min, and then incubated in a DMEM/F12 medium containing 1 µM polypeptide 1 or 4 at 37° C. for 10 min. Lactoferrin as a tear protein secreted in the medium was detected by westernblot, and quantified using human lactoferrin (Sigma-Aldrich Co.) as the standard. The collected medium was purified by 2D clean up kit (Bio-Rad Laboratories, Inc.), dissolved in NuPAGE LDS sample buffer (Invitrogen Corporation), and thermally denatured at 70° C. for 10 min. An equivalent amount of a sample was electrophoresed in 4-12% NuPAGE Bis Tris gel in MES buffer (Invitrogen Corporation) at 200 V for 35 min, and blotted on a PVDF membrane (Nihon Millipore K.K.) at 100 V for 60 min using Trans Blot Mini Cell (Bio-Rad Laboratories, Inc.). The membrane was blocked with TTBS (Bio-Rad Laboratories, Inc.) containing 5% skim-milk (Bio-Rad Laboratories, Inc.) at room temperature for 30 min, and reacted overnight at 4° C. with lactoferrin antibody (manufactured in rabbit, Sigma-Aldrich Co.) diluted 1000-fold. After washing the membrane with TTBS, the membrane was reacted at room temperature for 60 min with secondary antibody of anti-rabbit HRP, which was diluted 5000-fold. Then detection using ECL plus (GE healthcare) was performed. In addition, the amount of the secreted lactoferrin was quantified by forming an analytical curve of human lactoferrin on the same membrane, and comparing the density of the bands.

As shown in Table 3, polypeptide 1, which comprises the amino acid sequence of SEQ ID NO: 3, promoted the secretion of lactoferrin, which is one of the secretion markers of tear protein.

TABLE 3

| | amino acid No. in lacritin | number of amino acid residues | lactoferrin secretion amount (ng/10$^5$ cells) |
|---|---|---|---|
| polypeptide 1 | 68-102 | 35 | 11.7 |
| polypeptide 4 | 43-75 | 33 | 2.79 |

Formulation Example 1

Culture Medium for Preparation of Corneal Epithelial Sheet

Four milliliters of HCGS growth additive (contents: mEGF, hydrocortisone, insulin, transferrin and BPE, KURABO INDUSTRIES LTD. catalogue No.: KC-6150) and 15 mg of polypeptide 1 are added to EpiLife medium (corneal epithelial cell basal medium, Cascade Biologics, catalogue No.: M-EPI-500-CA) to give a culture medium (total amount 500 mL).

Formulation Example 2

Instillation Containing Lacritin Partial Peptide

The instillation shown below is prepared according to a conventional method.

| | |
|---|---|
| polypeptide 1 | 0.1 g |
| sodium dihydrogen phosphate | 0.1 g |
| sodium chloride | 0.9 g |
| sodium hydroxide | e.q. |
| sterilization purified water | e.q. |
| total amount | 100 mL (pH 7) |

This application is based on a patent application No. 2008-071065 filed in Japan, the contents of which are incorporated in full herein.

[Sequence Listing]

The invention claimed is:

1. An isolated polypeptide comprising the amino acid sequence of SEQ ID NO: 1 and having an amino acid length of not more than 70 residues.

2. A pharmaceutical product comprising the polypeptide of claim 1.

3. A method of promoting corneal epithelial cell adhesion, which method comprises contacting a corneal epithelial cell with an effective concentration of the polypeptide of claim 1, thereby promoting adhesion of the corneal epithelial cell.

4. The polypeptide according to claim 1, wherein the polypeptide comprises a partial sequence of the amino acid sequence of SEQ ID NO: 2.

5. A pharmaceutical product comprising the polypeptide of claim 4.

6. A method of promoting corneal epithelial cell adhesion, which method comprises contacting a corneal epithelial cell with an effective concentration of the polypeptide of claim 4, thereby promoting adhesion of the corneal epithelial cell.

7. The polypeptide according to claim 1, wherein the polypeptide consists of a partial sequence of the amino acid sequence of SEQ ID NO: 2.

8. A pharmaceutical product comprising the polypeptide of claim 7.

9. A method of promoting corneal epithelial cell adhesion, which method comprises contacting a corneal epithelial cell with an effective concentration of the polypeptide of claim 7, thereby promoting adhesion of the corneal epithelial cell.

10. An isolated polypeptide consisting of the amino acid sequence of any of SEQ ID NOs: 3-5.

11. A pharmaceutical product comprising the polypeptide of claim 10.

12. A method of promoting corneal epithelial cell adhesion, which method comprises contacting a corneal epithelial cell with an effective concentration of the polypeptide of claim 10, thereby promoting adhesion of the corneal epithelial cell.

13. The polypeptide of claim 10 consisting of the amino acid sequence of SEQ ID NO: 3.

14. A pharmaceutical product comprising the polypeptide of claim 13.

15. A method of promoting corneal epithelial cell adhesion, which method comprises contacting a corneal epithelial cell with an effective concentration of the polypeptide of claim 13, thereby promoting adhesion of the corneal epithelial cell.

16. The polypeptide of claim 10 consisting of the amino acid sequence of SEQ ID NO: 4.

17. A pharmaceutical product comprising the polypeptide of claim 16.

18. A method of promoting corneal epithelial cell adhesion, which method comprises contacting a corneal epithelial cell with an effective concentration of the polypeptide of claim 16, thereby promoting adhesion of the corneal epithelial cell.

19. The polypeptide of claim 10 consisting of the amino acid sequence of SEQ ID NO: 5.

20. A pharmaceutical product comprising the polypeptide of claim 19.

21. A method of promoting corneal epithelial cell adhesion, which method comprises contacting a corneal epithelial cell with an effective concentration of the polypeptide of claim 19, thereby promoting adhesion of the corneal epithelial cell.

* * * * *